United States Patent
Homan

(10) Patent No.: US 6,730,703 B2
(45) Date of Patent: May 4, 2004

(54) DUAL INHIBITORS OF CHOLESTERYL ESTER AND WAX ESTER SYNTHESIS FOR SEBACEOUS GLAND DISORDERS

(75) Inventor: Reynold Homan, Ann Arbor, MI (US)

(73) Assignee: Warner-Lambert Company, Morris Plains, NJ (US)

(*) Notice: Subject to any disclaimer, the term of this patent is extended or adjusted under 35 U.S.C. 154(b) by 35 days.

(21) Appl. No.: 10/182,847
(22) PCT Filed: Jan. 23, 2001
(86) PCT No.: PCT/US01/02190
§ 371 (c)(1), (2), (4) Date: Aug. 2, 2002
(87) PCT Pub. No.: WO01/56556
PCT Pub. Date: Aug. 9, 2001

(65) Prior Publication Data
US 2003/0060507 A1 Mar. 27, 2003

Related U.S. Application Data
(60) Provisional application No. 60/179,778, filed on Feb. 2, 2000.

(51) Int. Cl.[7] .................................................. A61K 31/18
(52) U.S. Cl. ........................ 514/602; 514/605; 514/864
(58) Field of Search ................................. 514/602, 605, 514/864

(56) References Cited

U.S. PATENT DOCUMENTS

| | | |
|---|---|---|
| 4,716,175 A | 12/1987 | Hoefle et al. |
| 4,722,927 A | 2/1988 | Holmes |
| 4,751,026 A | 6/1988 | Hoefle et al. |
| 4,868,210 A | 9/1989 | Trivedi |
| 4,923,896 A | 5/1990 | Trivedi |
| 4,948,806 A | 8/1990 | Trivedi |
| 4,994,465 A | 2/1991 | Trivedi |
| 4,999,373 A | 3/1991 | Trivedi |
| 5,015,644 A | 5/1991 | Roth et al. |
| 5,030,653 A | 7/1991 | Trivedi |
| 5,116,848 A | 5/1992 | Trivedi |
| 5,126,483 A | 6/1992 | Sekiya et al. |
| 5,155,127 A | 10/1992 | Trivedi |
| 5,202,351 A | 4/1993 | Sekiya et al. |
| 5,223,513 A | 6/1993 | Meguro et al. |
| 5,491,172 A | 2/1996 | Lee et al. |
| 5,565,472 A | 10/1996 | Hamanaka et al. |
| 5,596,001 A | 1/1997 | Hamanaka et al. |
| 5,656,634 A | 8/1997 | Chang et al. |

FOREIGN PATENT DOCUMENTS

| | | |
|---|---|---|
| EP | 0252524 A2 | 1/1988 |
| EP | 0399422 A1 | 11/1990 |
| EP | 0297610 B1 | 3/1991 |
| EP | 0293880 B1 | 8/1992 |
| EP | 0699439 A2 | 3/1996 |
| WO | 9104027 A1 | 4/1991 |
| WO | 9315058 A1 | 8/1993 |
| WO | 9324458 A1 | 12/1993 |

OTHER PUBLICATIONS

Reindel, James F. et al., Toxicologic Effects of a Novel Acyl–CoA: Cholesterol Acyltransfarase Inhibitor in Cynomolgus Monkeys, Toxicologic Pathology ISSN:0192–6233 Vol 22, No. 5, 1994 pp 510–518.

Primary Examiner—Vickie Kim
(74) Attorney, Agent, or Firm—J. Michael Dixon

(57) ABSTRACT

The present invention provides a method of treating sebaceous gland disorders comprising administering to a patient in need of said treatment an effective amount of a compound named [(2,4,6-triisopropyl-phenyl)-acetyl]-sulfamic acid 2,6-diiso-propyl-phenyl ester or a pharmaceutically acceptable salt thereof. Particularly, methods of treating sebaceous gland disorders are provided wherein said disorders are selected from seborrhea, acnes, perioral dermatitis, rosacea, and corticosteroid-induced acneiform lesions. The present invention provides methods of treating acnes such as, for example, chloracne, ciliaris acne, cystic acne, keratosa acne, vulgaris acne, senile acne, and medicinal acne.

3 Claims, 1 Drawing Sheet

DUAL INHIBITORS OF CHOLESTERYL ESTER AND WAX ESTER SYNTHESIS FOR SEBACEOUS GLAND DISORDERS

This application claims benefit of application Ser. No. 60/179,778 filed Feb. 2, 2000.

BACKGROUND OF THE INVENTION

The present invention relates to a method for using a compound named [(2,4,6-triisopropyl-phenyl)-acetyl]-sulfamic acid 2,6-diisopropyl-phenyl ester or a pharmaceutically acceptable salt thereof for the treatment of sebaceous gland disorders. Particularly, methods of treating sebaceous gland disorders are provided, wherein said disorders are selected from seborrhea, acnes, perioral dermatitis, rosacea, and corticosteroid-induced acneiform lesions.

Acne is a group of dermatological disorders which are associated with a variety of etiologies. The group of acnes includes chloroacne, ciliaris, cystic, keratosa, and vulgaris. In its vulgaris form, it occurs primarily in the face and trunk areas, affecting the appearance of the patient. It probably causes more mental pain and anguish to those afflicted than many other diseases which, from a physical standpoint, may be much more severe.

The basic lesion common to the family of diseases referred to as acnes is the comedo or "blackhead" of a pilosebaceous follicle. The condition may be mild and transient with only a few blackheads which can readily be ejected by pressure and are of little concern, or may be severe, persistent, and very disfiguring with the more serious cases causing cystic lesions and frequently leaving permanent scarring.

What appears to occur in the development of acnes is an initial filling up of the follicle with a viscous, keratinous material. This impaction of horny material is the whitehead and blackhead. As a result of bacterial growth in these horny impactions, the follicle ruptures initiating the inflammatory phase of the disease which takes the form of pustules, papules, cysts, and nodules. Although many different approaches have been used for the treatment of this affliction, none are universally effective and most possess undesirable side effects.

One of the commonly used methods for acne treatment is the use of "peeling," i.e., as astringent, agents for mild cases which cause exfoliation with the removal of some of the keratinous plugs. In the more serious cases where pustular or cystic lesions exists, the same are evacuated by incision and the contents expressed. Various other therapies have been employed, such as vaccine therapy, to assist in the control of chronic infection and increase the patient's resistance to Staphylococci; cortisone-type steroids; hormone therapy, which is applicable only for female patients who may be put on routine contraceptive regimen with estrogens; antibacterial therapy for the treatment of extensive pustular or cystic acne where the patient may be treated with tetracyclines, penicillin, erythromycin, or other of the antibacterial agents, and, in some instances, general surgical skin planing may be used. Systematic administration of hormones and antibacterials has been shown to have some therapeutic merit, but are unacceptable for chronic therapy.

The administration of large oral doses of vitamin A has been suggested as being beneficial in acne (Straumford J. V., "Vitamin A: Its Effects on Acne," *Northwest Med.*, August 1943;42:219–225), although other investigators have felt it to be ineffective (Anderson J. A. D. et al., "Vitamin A in Acne Vulgaris," *Brit. Med J.*, August 1963;2:294–296; Lynch F. W. et al., "Acne Vulgaris Treated With Vitamin A," *Arch Derm.*, March 1947;55:355, 357; and Mitchell G. H. et al., "Results of Treatment of Acne Vulgaris by Intramuscular Injections of Vitamin A," *Arch. Derm., October* 1951;64:428–430).

None of the common topical treatments has been found to be particularly effective. Vitamin A acid has been applied topically (Beer Von P., "Untersuchungen ber die Wirkung Vitamin A-Saure," *Dermatologica, March* 1962;124:192–195 and Stuttgen G., "Zur Lokalbehandlung von Keratosen mit Vitamin A-Saure," *Dermatologica,* February 1962;124:65–80) achieving good results in those hyperkeratotic disorders which are responsive to high oral doses of vitamin A. Among those treated by Beer and Stuttgen were patients with acne; however, these investigators reported no effective results on this disorder.

The treatment of acnes with isotretinoin and etretinate is described by Goldstein J. A. et al., "Comparative effect of sotretinoin and etretinate on acne and sebaceous gland secretion," *J. Am Acad Dermatol,* 1982;6:760765. Shapiro S. S. et al., discuss treatment of acnes with various potential therapeutic entities in "Evaluation of Potential Therapeutic Entities for the Treatment of Acne" *Pharmacology of Retinoids in the Skin. Pharmacol. Skin.* Reichert and Shroot, eds, Karger, Basel, 1989;3:104–122.

Lambert R. W. and Smith R. E. have discussed the "[e]ffects of 13-cis-retinoic acid on the hamster Meibomian gland," *J. Invest Derm,* 1989;93(2):321–325 whereas the effects of retinoids on psoriasis is discussed by Lowe N. J. and David M. in "Systemic Retinoids in Psoriasis: Comparative Efficacy and Toxicity," *Pharmacology of Retinoids in the Skin. Pharmacol. Skin,* Reichert and Shroot eds, Karger, Basel, 1989;3:104–122.

U.S. Pat. No. 3,729,568 refers to the use of vitamin A acid (retinoic acid or tretinoin) in the treatment of acne vulgaris.

International Patent Application PCT/US92/06485 teaches the use of vitamin A acid derivatives in the treatment of skin diseases including acne.

U.S. Pat. No. 4,703,110 describes the use of para substituted benzoic acid derivatives in the treatment of dermatological disorders including cystic acne.

U.S. Pat. No. 4,927,928 teaches the use of benzamido compounds in the treatment of dermatological diseases having an inflammatory and/or immunoallergic component, including acne vulgaris, senile acne, and medicinal or professional acne.

U.S. Pat. No. 4,716,175 granted Dec. 29, 1987, discloses ACAT inhibitors which include the compound named 2,2-dimethyl-N-(2,4,6-trimethoxyphenyl)-dodecanamide. The compound has the following structure:

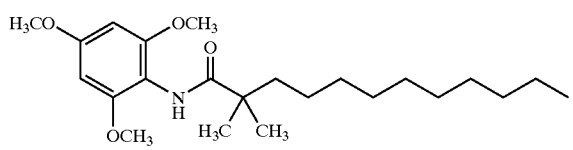

This patent is hereby incorporated by reference.

European Patent Application Number EP0699439A2 discloses ACAT inhibitors useful for the treatment of sebaceous gland disorders, particularly acne. This application is incorporated herein by reference. The instant compound [(2,4,6-triisopropyl-phenyl)-acetyl]-sulfamic acid 2,6-diisopropyl-phenyl ester is not disclosed in EP0699439A2 or in references recited therein.

Compounds that inhibit acyl-coenzyme A: cholesteryl acyltransferase are known as ACAT inhibitors. An ACAT inhibitor, which is [(2,4,6-triisopropyl-phenyl)-acetyl]-sulfamic acid 2,6-diisopropyl-phenyl ester and the methods for preparing it, are taught in U.S. Pat. No. 5,491,172 and its divisional 5,633,287, which are hereby incorporated by reference. The compound named [(2,4,6-triisopropyl-phenyl)-acetyl]-sulfamic acid 2,6-diisopropyl-phenyl ester is also known by the generic name avasimibe. The use of the compound taught is for treatment of hypercholesterolemia and atherosclerosis.

Methods of using [(2,4,6-triisopropyl-phenyl)-acetyl]-sulfamic acid 2,6-diisopropyl-phenyl ester for lowering Lp(a) levels is taught in U.S. Pat. No. 6,117,909.

Methods of using [(2,4,6-triisopropyl-phenyl)-acetyl]-sulfamic acid 2,6-diisopropyl-phenyl ester for prevention of plaque rupture is taught in co-pending patent application Ser. No. 60/163,814 filed Nov. 5, 1999.

We have now discovered a surprising and beneficial result. Administration of [(2,4,6-triisopropyl-phenyl)-acetyl]-sulfamic acid 2,6-diisopropyl-phenyl ester inhibits wax ester synthesis. Thus [2,4,6-triisopropyl-phenyl)-acetyl]-sulfamic acid 2,6-diisopropyl-phenyl ester has now been discovered to have unexpected benefits useful for the treatment of sebaceous gland disorders, particularly acnes, perioral dermatitis, rosacea, and corticosteroid-induced acneiform lesions. The acne is selected from, for example, chloracne, ciliaris acne, cystic acne, keratosa acne, vulgaris acne, senile acne, and medicinal acne.

SUMMARY OF THE INVENTION

The present invention provides a method of treating sebaceous gland disorders comprising administering to a patient in need of said treatment an effective amount of a compound named [(2,4,6-triisopropyl-phenyl)-acetyl]-sulfamic acid 2,6-diisopropyl-phenyl ester or a pharmaceutically acceptable salt thereof. It is also understood that the present invention provides a method of treating sebaceous gland disorders in a mammal, especially a human, comprising administering a therapeutically effective amount of a compound named [(2,4,6-triisopropyl-phenyl)-acetyl]-sulfamic acid 2,6-diisopropyl-phenyl ester and pharmaceutically acceptable salts thereof.

Particularly, the present invention provides a method of treating sebaceous gland disorders wherein said disorders are selected from acnes, perioral dermatitis, rosacea, and corticosteroid-induced acneiform lesions. The present invention especially provides methods of treating acnes such as, for example, chloracne, ciliaris acne, cystic acne, keratosa acne, vulgaris acne, senile acne, and medicinal acne.

DETAILED DESCRIPTION OF THE INVENTION

Figure 1:
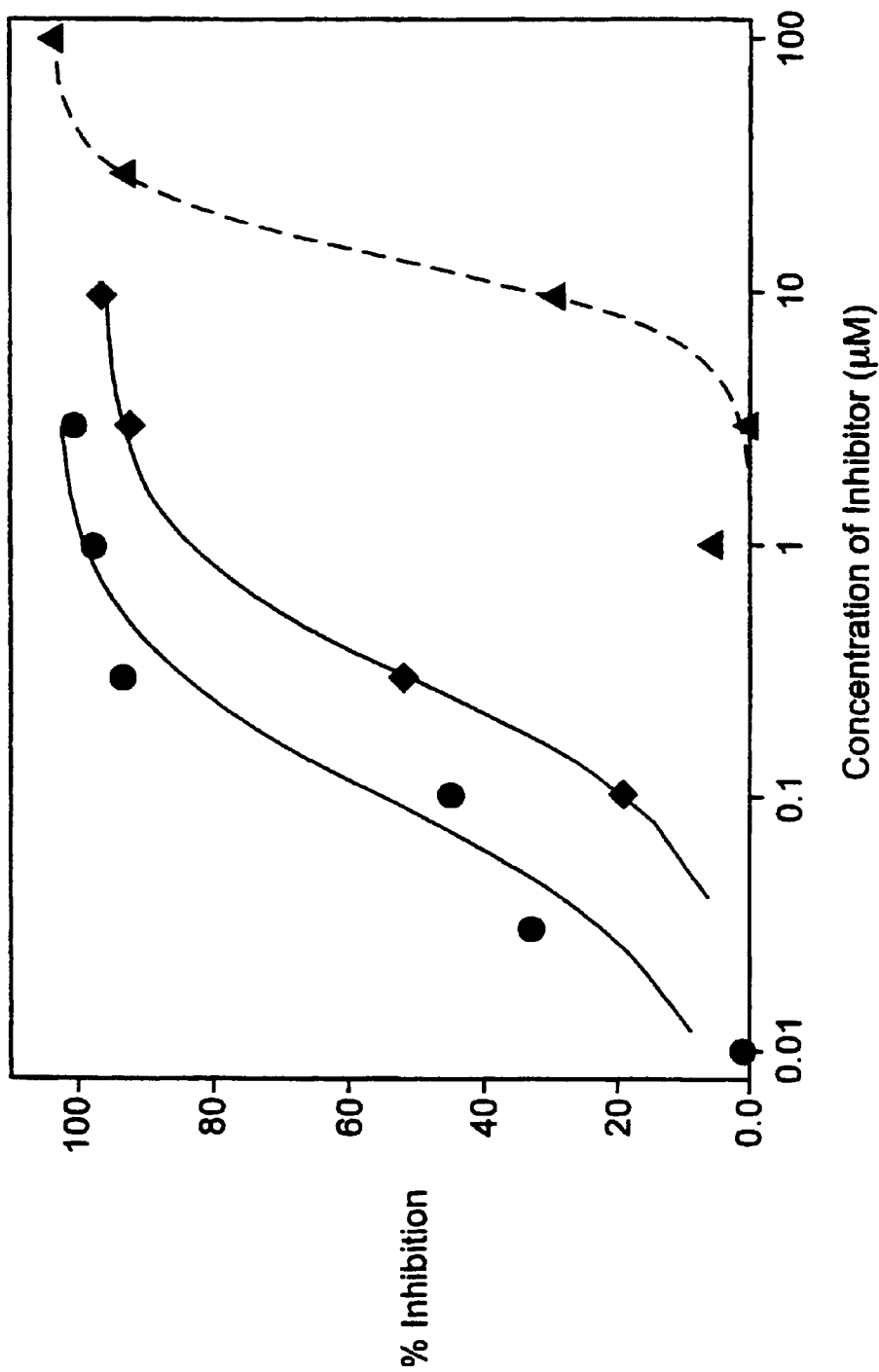
FIG. 1 is a line graph of the percent inhibition of cholesteryl ester and wax ester synthesis in mouse preputial gland and liver microsomes versus inhibitor concentration for [(2,4,6-triisopropyl-phenyl)-acetyl]-sulfamic acid 2,6-diisopropyl-phenyl ester and 2,2-dimethyl-N-(2,4,6-trimethoxyphenyl)-dodecanamide.

The present invention provides a method of treating sebaceous gland disorders comprising administering to a patient in need of said treatment an effective amount of a compound named [(2,4,6-triisopropyl-phenyl)-acetyl]-sulfamic acid 2,6-diisopropyl-phenyl ester or a pharmaceutically acceptable salt thereof. The compound [(2,4,6-trisopropyl-phenyl)-acetyl]-sulfamic acid 2,6-diisopropyl-phenyl ester, also known by its generic name avasimibe, was first taught in U.S. Pat. No. 5,491,172 and the divisional patent, U.S. Pat. No. 5,633,287. Avasimibe or the compound of Formula I has the following structure:

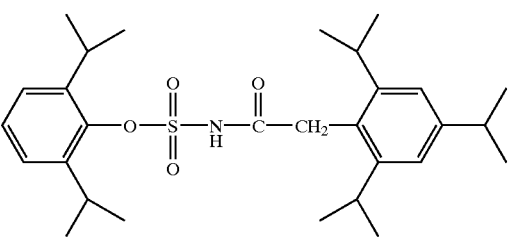

The present invention provides a method of treating sebaceous gland disorders in a mammal, especially a human, comprising administering a therapeutically effective amount of a compound of Formula I named [(2,4,6-triisopropyl-phenyl)-acetyl]-sulfamic acid 2,6-diisopropyl-phenyl ester or a pharmaceutically acceptable salt thereof.

Further, the present invention provides methods of treating sebaceous gland disorders as described above wherein said disorders are selected from seborrhea, acnes, perioral dermatitis, rosacea, or corticosteroid-induced acneiform lesions.

The present invention provides methods of treating sebaceous gland disorders as described above wherein said disorders are selected from chloracne, ciliaris acne, cystic acne, keratosa acne, vulgaris acne, senile acne, or medicinal acne.

A preferred embodiment of the present invention provides methods of treating acnes as described above wherein said acne is selected from chloracne, ciliaris acne, cystic acne, keratosa acne, vulgaris acne, senile acne, or medicinal acne.

The present invention further provides a method of inhibiting sebum production in a human in need of said treatment comprising administering to said human a sebum production-inhibiting amount of [(2,4,6-triisopropyl-phenyl)-acetyl]-sulfamic acid 2,6-diisopropyl-phenyl ester or a pharmaceutically acceptable salt thereof. Such method is useful to treat any of the sebaceous gland disorders cited above, or to treat or prevent other conditions caused by overproduction of sebum such as oily skin. In a preferred embodiment, the compound is administered topically.

The present invention also provides a pharmaceutical composition comprising a sebaceous gland secretion inhibiting amount of compound named [(2,4,6-triisopropyl-phenyl)-acetyl]-sulfamic acid 2,6-diisopropyl-phenyl ester and a pharmaceutically acceptable carrier.

The present invention further provides a pharmaceutical composition comprising an acne-inhibiting amount of a compound named [(2,4,6-triisopropyl-phenyl)-acetyl]-sulfamic acid 2,6-diisopropyl-phenyl ester and a pharmaceutically acceptable carrier. Additionally, the present invention provides a pharmaceutical composition comprising an acne-inhibiting amount of an ACAT inhibitor named [(2,4,6-triisopropyl-phenyl)-acetyl]-sulfamic acid 2,6-diisopropyl-phenyl ester and a pharmaceutically acceptable carrier.

The present invention also provides a method of treating acnes comprising administering to a patient in need of said treatment an acne-inhibiting amount of a compound named [(2,4,6-triisopropyl-phenyl)-acetyl]-sulfamic acid 2,6-diisopropyl-phenyl ester or a pharmaceutically acceptable salt thereof. Further provided by the present invention is a method of treating acnes comprising administering to a patient in need of said treatment a pharmaceutical composition comprising an acne-inhibiting amount of a compound named [(2,4,6-triisopropyl-phenyl)-acetyl]-sulfamic acid 2,6-diisopropyl-phenyl ester and a pharmaceutically acceptable carrier. Still further, the present invention provides the use of a compound named [(2,4,6-triisopropyl-phenyl)-acetyl]-sulfamic acid 2,6-diisopropyl-phenyl ester for the manufacture of a medicament for the treatment of acnes.

Furthermore, the present invention provides the use of a compound named [(2,4,6-triisopropyl-phenyl)-acetyl]-sulfamic acid 2,6-diisopropyl-phenyl ester for the manufacture of a medicament for the treatment of diseases caused by sebaceous gland disorders. Still further provided by the present invention is the use of a compound named [(2,4,6-triisopropyl-phenyl)-acetyl]-sulfamic acid 2,6-diisopropyl-phenyl ester for the manufacture of a pharmaceutical composition for the treatment of diseases caused by sebaceous gland disorders, including acnes, in a patient in need of said treatment.

The present invention further provides the use of [(2,4,6-triisopropyl-phenyl)-acetyl]-sulfamic acid 2,6-diisopropyl-phenyl ester or a pharmaceutically acceptable salt thereof in the manufacture of a medicament that can inhibit sebum production in a human. In a preferred embodiment, the medicament is adapted for topical application.

Additionally, the present invention provides a method of inhibiting AFAT comprising administering to a patient in need of said treatment an AFAT inhibiting amount of a compound named [(2,4,6-triisopropyl-phenyl)-acetyl]-sulfamic acid 2,6-diisopropyl-phenyl ester or a pharmaceutically acceptable salt thereof.

The present invention also provides a method of inhibiting ACAT and AFAT comprising administering to a patient in need of said treatment an ACAT and AFAT inhibiting amount of a compound named [(2,4,6-triisopropyl-phenyl)-acetyl]-sulfamic acid 2,6-diisopropyl-phenyl ester.

Avasimibe has shown an unexpected ability to inhibit sebaceous gland secretions. This activity is beneficial for the treatment of sebaceous gland disorders wherein one component of said disorders is characterized by excessive secretion of sebum. Thus, avasimibe is useful in the treatment of, inter alia, acnes, perioral dermatitis, rosacea, and corticosteroid-induced acneiform lesions in patients suffering therefrom.

Avasimibe is especially useful for the treatment of acnes, which include chloracne, ciliaris acne, cystic acne, keratosa acne, vulgaris acne, senile acne, and medicinal acne. Acne is a skin disease suffered by many adults and most adolescents. Avasimibe is therefore expected to benefit a substantial number of people.

As used herein, the term "AFAT" means acyl-Coenzyme A: fatty alcohol acyltransferase.

The term "ACAT" means acyl-Coenzyme A: cholesteryl acyltransferase.

The term "patient" means a mammal, which includes a human.

The term "wax ester" means an ester formed from a fatty acid and a long chain alcohol, also known as fatty alcohol.

The term "cholesteryl ester" means an ester formed from a fatty acid and cholesterol.

The term "sebum" means a secretion of the sebaceous gland comprising, inter alia, triglycerides, free fatty acids, wax esters, squalene, cholesteryl, and cholesteryl esters.

The compound of the invention is capable of further forming pharmaceutically acceptable salts, such as pharmaceutically acceptable base addition salts. Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M. et al., "Pharmaceutical Salts," *J. of Pharma. Sci.*, 1977;66:1). All of these forms are within the scope of the present invention.

The base addition salts of said acidic compound are prepared by contacting the free acid form with a sufficient amount of the desired base to produce the salt in the conventional manner. The free acid form may be regenerated by contacting the salt form with an acid and isolating the free acid in the conventional manner. The free acid form differs from its respective salt forms somewhat in certain physical properties such as solubility in polar solvents, but otherwise the salts are equivalent to their respective free acid for purposes of the present invention.

The compound of the present invention can exist in unsolvated forms as well as solvated forms, including hydrated forms. In general, the solvated forms, including hydrated forms, are equivalent to unsolvated forms and are encompassed within the scope of the present invention.

The compound of the present invention can be prepared and administered in a wide variety of oral and parenteral dosage forms. Thus, the compound of the present invention can be administered by injection, that is, intravenously, intramuscularly, intracutaneously, subcutaneously, intraduodenally, or intraperitoneally. Also, the compound of the present invention can be administered by inhalation, for example, intranasally. Additionally, the compound of the present invention can be administered transdermally. It will be obvious to those skilled in the art that the following dosage forms may comprise as the active component, either the compound of Formula I or a corresponding pharmaceutically acceptable salt of the compound of Formula I.

For preparing pharmaceutical compositions from the compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Also included are topical form preparations such as gels, creams, lotions, solutions, ointments, and the like. Also included are topical form preparations such as jellies, pastes, ointments, salves and the like. Topical form preparations may be prepared by combining one or more film-forming agents and the active component in finely divided form or in solution. Film-forming agents include, stearyl alcohol, cetyl alcohol, propylene glycol, glycerine, carboxymethylcellulose, hydroxyethyl cellulose, and the like and are well-known to one skilled in the art.

Examples of vehicles for application of the active compounds of this invention include an aqueous or water-alcohol solution, an emulsion of the oil-in-water or water-in-oil type, an emulsified gel, or a two-phase system. Preferably, the compositions according to the invention are in the form of lotions, creams, milks, gels, masks, microspheres or nanospheres, or vesicular dispersions. In the case of vesicular dispersions, the lipids of which the vesicles are made can be of the ionic or nonionic type, or a mixture thereof.

In addition to the above-mentioned film-forming agents, various other ingredients can be incorporated into the compositions of this invention for topical administration to improve their therapeutic efficacy and stability. These include antiseptics such as benzyl alcohol and suitable skin-permeation enhancing adjuvants like diethyl sebecate and the like. These ingredients are well-known to one skilled in the art.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents for the treatment of sebaceous gland disorders, the compounds utilized in the pharmaceutical method of this invention can be administered at the initial dosage of about 1 mg to about 100 mg per kilogram daily. As such, an effective amount, an acne-inhibiting amount, a sebaceous gland secretion-inhibiting amount, an AFAT inhibiting amount, and an ACAT and AFAT inhibiting amount will generally vary from about 1 mg to about 100 mg per kilogram of body weight per day. A daily dose range of about 25 mg to about 75 mg per kilogram is preferred.

In determining the effective amount, the acne-inhibiting amount, the sebaceous gland secretion-inhibiting amount, the sebum production-inhibiting amount, the AFAT inhibiting amount, and the ACAT and AFAT inhibiting amount a number of factors are to be considered by the attending diagnostician. As such, the dosages may be varied depending upon the requirements of the patient, the severity of the condition being treated, and the formulation of the compound employed. Determination of the proper dosage for a particular situation is within the skill of the art. Generally, treatment is initiated with smaller dosages that are less than the optimum dose of the compound. Thereafter, the dosage is increased by small increments until the optimum effect under the circumstance is reached. For convenience, the total daily dosage may be divided and administered in portions during the day if desired.

An example of an oral formulation follows.

Tablet Formulation:

| Ingredient | Amount (mg) |
| --- | --- |
| [(2,4,6-triisopropyl-phenyl)-acetyl]-sulfamic acid, 2,6-diisopropyl-phenyl ester | 25 |
| Lactose | 50 |
| Cornstarch (for mix) | 10 |
| Cornstarch (paste) | 10 |
| Magnesium stearate (1%) | 5 |
| Total | 100 |

The sulfamic acid, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a patient, such as a human from one to four times a day for treatment of sebaceous gland disorders.

An oral solution is prepared having the following formula:

Oral Solution:

| Ingredient | Percent by Weight |
|---|---|
| [(2,4,6-triisopropyl-phenyl)-acetyl]-sulfamic acid, 2,6-diisopropyl-phenyl ester | 2.0 |
| Ethyl alcohol | 10.0 |
| Benzyl alcohol | 1.0 |
| Peppermint flavor | 0.2 |
| Vanillin | 0.2 |
| Polysorbate 40 | 0.1 |
| Sucrose | 50.0 |
| Purified water | Balance |

The ingredients are combined and mixed to form a uniform solution.

A gel is prepared having the following composition:

Topical Gel:

| Ingredient | Percent by Weight |
|---|---|
| [(2,4,6-triisopropyl-phenyl)-acetyl]-sulfamic acid, 2,6-diisopropyl-phenyl ester | 0.50 |
| Propylene glycol | 20.00 |
| Ethanol | 20.00 |
| Carboxyvinyl polymer [Carbomer 940 (trademark)] | 1.00 |
| Hydroxyethyl cellulose | 0.40 |
| Benzyl alcohol | 1.00 |
| Sodium hydroxide 1N | to pH 6 |
| Distilled water | Balance |

The components other than sodium hydroxide are combined to yield a homogeneous dispersion. Addition of sodium hydroxide causes the mixture to gel yielding a ready-to-use semisolid.

A cream is prepared consisting of:

Topical Cream:

| Ingredient | Percent by Weight |
|---|---|
| [(2,4,6-triisopropyl-phenyl)-acetyl]-sulfamic acid, 2,6-diisopropyl-phenyl ester | 0.50 |
| Stearic acid | 7.00 |
| Stearyl alcohol | 5.00 |
| Cetyl alcohol | 2.00 |
| Glycerin | 10.00 |
| Sodium laurylsulfate | 1.00 |
| Propylparaben | 0.05 |
| Methylparaben | 0.25 |
| Disodium edetate | 0.05 |
| Distilled water | Balance |

The first four ingredients are heated to approximately 70° C. to produce a uniform melt. The remaining ingredients are combined, heated to approximately 75° C., and added, with mixing, to the previously prepared melt. The emulsion, thus formed, is subsequently homogenized and cooled to yield a smooth white cream.

A lotion is prepared having the following composition:

Topical Lotion:

| Ingredient | Percent by Weight |
|---|---|
| [(2,4,6-triisopropyl-phenyl)-acetyl]-sulfamic acid, 2,6-diisopropyl-phenyl ester | 0.50 |
| Glyceryl mnonostearate | 1.00 |
| Isopropyl palmitate | 4.00 |
| Polyethylene glycol 400 distearate | 2.00 |
| Glycerin | 10.00 |
| Methylparaben | 0.10 |
| Sodium cetylsulfate | 5.00 |
| Distilled water | Balance |

The first four ingredients are combined and heated to approximately 70° C., then added with agitation to a mixture of the remaining ingredients, also at about 70° C. The emulsion is appropriately homogenized and cooled to produce a smooth, white, pourable lotion.

A topical solution is prepared having the following composition:

Topical Solution:

| Ingredient | Percent by Weight |
|---|---|
| [(2,4,6-triisopropyl-phenyl)-acetyl]-sulfamic acid, 2,6-diisopropyl-phenyl ester | 0.50 |
| Propylene glycol | 20.00 |
| Ethanol | 50.00 |
| Benzyl alcohol | 1.00 |
| Disodium edetate | 0.01 |
| Propyl gallate | 0.10 |
| Citric acid | 0.20 |
| Sodium hydroxide 1N | to pH 6 |
| Distilled water | Balance |

All ingredients except sodium hydroxide are combined with agitation, and the pH of the resultant solution is adjusted with 1N sodium hydroxide, to pH 6, to yield a free-flowing, quick-drying topical solution.

Materials and methods of the instant invention are as follows:
I. Preparation of Microsomes
Solutions:
A. Wash buffer (300 mM Sucrose, 5 mM DTT) 102.7 g sucrose+0.77 g dithiothreitol (DTT)+water to 1 L.
B. Homogenizing buffer (Wash buffer with leupeptin and ethylene glycol-bis (β-aminoethyl ether) tetra-acetic acid [EGTA]). Prepare wash buffer as above including 25 mg leupeptin and 380 mg EGTA.
C. Phosphate Buffer (0.2 M, pH 7.4) Combine 100 mL 1 M $KH_2PO_4$ with 100 mL 3 M $K_2HPO_4$ and bring to 1000 mL with water. Check pH and adjust to pH 7.4 with either 0.1 N $H_3PO_4$ or 0.1 N KOH.
Microsome Isolation
Preputial Gland (PG) Removal from Rat or Mouse
a) The rats or mice are anesthetized with ether, and the PGs are removed and placed in a beaker containing wash buffer (ice cold).
b) As soon as possible, the PGs are homogenized in a Potter-Elvehjem homogenizer with 15 mL of homogenizing buffer. The homogenizer is kept in a small ice bath. Work the plunger until it reaches the bottom of the tube 10 times.

c) Dilute with homogenizing buffer to a volume of 200 mL.
d) Pour homogenate into 15×100 mm sorvall tubes in an ice bath. Each tube holds 13.5 mL to the mark.
e) Spin in Sorvall Centrifuge at 5° C., 10,000 rpm (12,000× G) for 15 minutes.
f) Remove the fats floating on the top with the flat blade of a spatula and decant the supernatant into fresh tubes.
g) Repeat Steps e and f.
h) Carefully transfer as much of the supernatant as possible without disturbing the debris at the bottom of the tube to ultracentrifuge bottles for 50 Ti or 60 Ti Beckman Ultracentrifuge rotor. The tubes are kept in an ice bath.
i) Centrifuge in the Beckman Ultracentrifuge at 105,000×g for 1 hour at 14° C.
j) Discard supernatant.
k) Add 1 mL of 0.2 M $KPO_4$ buffer pH 7.4 to half of the bottles in an ice bath. Scrape the whole pellet loose with a teflon rod and transfer to a 15 mL homogenizer. Wash bottle with 1 mL of buffer and transfer to one of the bottles that has a pellet but no buffer. Homogenize gently by hand. Aliquot into Cryovials (Nalgene™) and store in liquid nitrogen. The microsomes remain active for at least 2 years.
m) Determine the protein concentration of the homogenate by the Lowry method. Dilute 20 $\mu$L with 180 $\mu$L saline and assay 2×10 $\mu$L and 2×20 $\mu$L. Note: $KPO_4$ will cause a precipitate to form during the Lowry procedure (Lowry O. H., Rosebrough N. T., Farr A. I. and Randal R. J., *J. Biol. Chem.*, 1951;193:265–275). Desired protein concentration is 20 mg/mL rat or mouse PG microsomes.

II. ACAT Assay
Solutions
A. Sucrose Buffer (300 mM Sucrose, 40 mM $KH_2PO_4$, 50 mM KCl, 30 mM EDTA, pH 7.4). Prepare 1 M phosphate buffer. Dissolve 70.89 g $K_2HPO_4$ and 12.65 g $KH_2PO_4$ in 480 mL water. Adjust pH to 7.4 with KOH or $H_3PO_4$ as needed. Adjust volume to 500 mL with water. Combine 20 mL 1 M phosphate buffer with 1.865 g KCl, 51.35 g sucrose, and 5 mg EDTA. Adjust volume to 480 mL with water, adjust pH to 7.4 as above and bring to 500 mL with water. Pass final solution through 0.45 $\mu$m filter sterilization unit (e.g., Nalgene 450–0045).
B. 1% methyl-$\beta$-cyclodextrin: 10 mL sucrose buffer plus 100 mg methyl-$\beta$-cyclodextrin.
C. [4-$^{14}$C]Cholesteryl or [1-$^{14}$C]Hexadecanol. Evaporate the toluene from the vial. Re-suspend radiolabel in 0.1 mL 2-propanol.
D. Oleoyl Coenzyme A (1 mM in sucrose buffer). Dissolve 10.3 mg oleoyl coenzyme A (Sigma 0–7002) in 10 mL sucrose buffer. Note: Store at –10° C. Dilute 5-fold to 200 $\mu$M with sucrose buffer just prior to assay.
E. [$^{14}$C]Cholesteryl—Labeled Microsomes or [$^{14}$C]Hexadecanol—Labeled Microsomes. Dilute a vial of stock microsomes to 4 mg protein per milliliter with sucrose buffer. For every 1 mL of diluted microsome solution, use glass syringe (Hamilton, GASTIGHT, 1702) and transfer 2.5 $\mu$L of radiolabel to diluted microsomes by submerging syringe needle in the microsome solution and swirling while ejecting syringe contents. Flush syringe once with microsome solution. Determine dpm in small aliquot of solution by liquid scintillation counting (LSC). Need approximately 4×10$^6$ dpm/mL in the microsome solution.
F. Acid Quench Solution (0.5% $H_2SO_4$). Add 0.5 mL 36N $H_2SO_4$ (concentrated) to 100 mL water.
G. Test Compound Solutions. Test compounds are weighed to make either 1 mM or 4 mM stock solutions in dimethylsulfoxide (DMSO). These solutions are used to prepare DMSO solutions containing 40 times the concentration of compound to be tested. These solutions may be prepared 24 hours prior to the assay and stored at room temperature.

ACAT
Assay Procedure
a) Duplicate samples are prepared by adding 5 $\mu$L of test compound solution to each of two assay tubes. Controls and blanks receive 5 $\mu$L of DMSO. Control and blank samples do not contain inhibitor. Note: Incubations are performed in 110×17 mm, polypropylene, conical bottom tubes (Thermowells).
b) Add 100 $\mu$L of 1% m$\beta$CD solution to each tube.
c) Add 20 $\mu$L of desired concentration (mg/mL) radiolabeled microsomes to each tube.
d) Incubate assay tubes in a 37° C. shaking water bath for 30 minutes.
e) Start the reaction by adding 10 $\mu$L of 299 $\mu$M oleoyl coenzyme A to all tubes EXCEPT THE BLANKS.
f) 10 $\mu$L of sucrose buffer is added to the blanks.
g) Three minutes after the oleoyl coenzyme A addition, stop the reaction by adding 10 $\mu$L of the $H_2SO_4$ quench solution.
h) Transfer 40 $\mu$L of the acidified solution to the pre-absorbent area of Whatman LK6D silica gel TLC plates, which are then dried on a hot plate for 5 minutes and developed in trimethylpentane/diethyl ether/acetic acid (75:25:2). The bands containing radiolabel are detected and quantitated by phosphorimaging with a Molecular Dynamics phosphorimager.

III. Data Analysis and Statistical Evaluation
TLC will resolve free alcohol from its ester. The relative amount of radioactivity in each of those bands is determined by phosphorimaging. This data is used to calculate fraction of ester formed as E/E+A where, $$(\% \text{ Inhibition} = [(Ec/Ec+Ac)-(Et/Et+At)]\times(Ec+Ac/Ec)\times 100)$$

Where, E=Ester band intensity and A=Alcohol band intensity. The concentration of inhibitor producing 50% inhibition ($IC_{50}$) is calculated by a nonlinear least squares fit of the data to the logistic function:

$$Y=100/1+(X/C)^b$$

Where Y is percent inhibition, X is the inhibitor concentration, C is the $IC_{50}$, and b is an independent fitting parameter.

For this study, we are assuming
That the population distribution is at least approximately normal.
If $X_1, X_2, \ldots X_N$ is a random sample from a normal distribution, the standardized variable, $$T = \frac{x-\mu}{S/\sqrt{n}}$$

has a t distribution with n–1 degrees of freedom.
–$H_o$: $\mu=\mu_o$
–$H_a$: $\mu<\mu_o$ against the test statistic T.
When $H_o$ is true, the test statistic has a t distribution with n–1 degrees of freedom. Knowledge of the test statistic's distribution when $H_o$ is true (the "null distribution") allows construction of a rejection region for which the type I error probability is controlled at the desired level.

$$P(\text{type } I \text{ error})=P(H_o \text{ is rejected when it is true})=\alpha.$$

The experimental results for inhibition of cholesteryl ester (CE) and wax ester (WE) synthesis by [(2,4,6-triisopropyl-phenyl)-acetyl]-sulfamic acid 2,6-diisopropyl-phenyl ester (compound 1) and 2,2-dimethyl-N-(2,4,6-trimethoxyphenyl)-dodecanamide (compound 2) are recited in Table 1 and FIG. 1. The data for CE synthesis inhibition was generated using a mouse liver microsome preparation. The data for WE synthesis inhibition was generated using a mouse preputial microsome preparation. Data in Table 1 are given as an $IC_{50}$, which is the concentration of inhibitor in micromolar required to inhibit the synthesis by 50%.

TABLE 1

Inhibition of Cholesteryl Ester (CE) and Wax Ester (WE) Synthesis

| Compound No. | $IC_{50}$ ($\mu$M) | |
|---|---|---|
| | CE | WE |
| 1 | 0.09 | 13.9 |
| 2 | 0.27 | >100 |

For each compound, the difference between wax ester synthesis inhibition and cholesteryl ester synthesis inhibition indicates separate enzymes are responsible for wax ester synthesis and cholesteryl ester synthesis. The data further demonstrate that compounds designed as inhibitors of ACAT are not necessarily inhibitors of AFAT, as shown by the results for compound 2. The data for avasimibe (compound 1) provide the first description of an established ACAT inhibitor that is also capable of inhibiting AFAT. Such surprising dual inhibitory activity is beneficial in the treatment of sebaceous gland disorders because the wax ester and cholesteryl ester products of AFAT and ACAT, respectively, form a major portion of the sebum, which is secreted in excess by the sebaceous gland during episodes of seborrhea and the associated acne. In summary, the data presented in Table 1 and FIG. 1 demonstrate that avasimibe is the first and only compound shown to date to inhibit both ACAT and AFAT. The unexpected dual inhibition of AFAT and ACAT by avasimibe provides benefits to patients suffering from disorders characterized by excess sebum secretion that are not provided by compounds that only inhibit ACAT.

DETAILED DESCRIPTION OF THE DRAWING

FIG. 1 is a line graph of the percent inhibition of cholesteryl ester (CE) synthesis in mouse liver microsomes by 2,2-dimethyl-N-(2,4,6-trimethoxyphenyl)-dodecanamide (compound 2) and the percent inhibition of wax ester (WE) synthesis in mouse preputial gland microsomes and CE synthesis in mouse liver microsomes by [(2,4,6-triisopropyl-phenyl)-acetyl]-sulfamic acid 2,6-diisopropyl-phenyl ester (compound 1) versus inhibitor concentration from 0.01 $\mu$M to 100 $\mu$M. Due to an $IC_{50}$>100 $\mu$M, inhibition of WE synthesis in mouse preputial gland microsomes by compound 2 could not be depicted in FIG. 1.

In FIG. 1:

▲ denotes inhibition data points of wax ester synthesis in mouse preputial gland microsomes for [(2,4,6-triisopropyl-phenyl)-acetyl]-sulfamic acid 2,6-diisopropyl-phenyl ester (compound 1), ● denotes inhibition data points of cholesteryl ester synthesis in mouse liver microsomes for [(2,4,6-triisopropyl-phenyl)-acetyl]-sulfamic acid 2,6-diisopropyl-phenyl ester (compound 1), and ◇ denotes inhibition data points of cholesteryl ester synthesis in mouse liver microsomes for 2,2-dimethyl-N-(2,4,6-trimethoxyphenyl)-dodecanamide (compound 2).

The inhibition curves in FIG. 1 show that both compounds 1 and 2 are potent inhibitors of rat liver ACAT. However, while compound 2 showed no inhibition of WE synthesis in mouse preputial gland microsomes, compound 1 unexpectedly inhibits WE synthesis, having an $IC_{50}$=13.9 $\mu$M.

What is claimed is:

1. A method of treating sebaceous gland disorders comprising administering to a patient in need of said treatment an effective amount of a compound named [(2,4,6-triisopropyl-phenyl)-acetyl]-sulfamic acid 2,6-diisopropyl-phenyl ester or a pharmaceutically acceptable salt thereof wherein the sebaceous gland disorder is selected from the group consisting of seborrhea and rosacea.

2. A method according to claim 1 wherein said disorder is seborrhea.

3. A method according to claim 1 wherein said disorder is rosacea.

* * * * *